(12) United States Patent
Papac et al.

(10) Patent No.: US 8,662,670 B2
(45) Date of Patent: Mar. 4, 2014

(54) SPECTRALLY-ADJUSTABLE OPHTHALMIC ILLUMINATION WITH DISCRETE SOURCES

(75) Inventors: Michael Papac, Tustin, CA (US); Ronald T. Smith, Irvine, CA (US); Michael J. Yadlowsky, Irvine, CA (US); Alexander N. Artsyukhovich, San Juan Capistrano, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 117 days.

(21) Appl. No.: 13/076,570

(22) Filed: Mar. 31, 2011

(65) Prior Publication Data

US 2011/0292343 A1 Dec. 1, 2011

Related U.S. Application Data

(60) Provisional application No. 61/349,316, filed on May 28, 2010.

(51) Int. Cl.
| | |
|---|---|
| *A61B 3/00* | (2006.01) |
| *A61B 19/00* | (2006.01) |
| *A61B 18/18* | (2006.01) |
| *A61N 5/06* | (2006.01) |
| *A61N 1/30* | (2006.01) |

(52) U.S. Cl.
USPC .......... 351/221; 351/205; 607/88; 128/898; 606/4; 606/21

(58) Field of Classification Search
USPC ............. 351/221, 200, 205, 213; 606/2–19; 128/898; 362/572; 607/88–95; 600/156–183; 604/4, 21
See application file for complete search history.

(56) References Cited

U.S. PATENT DOCUMENTS

| | | |
|---|---|---|
| 6,183,086 B1 | 2/2001 | Neubert |
| 2008/0246920 A1 * | 10/2008 | Buczek et al. ................ 351/221 |

OTHER PUBLICATIONS

Papac et al.; U.S. Appl. No. 13/076,639, filed Mar. 31, 2011; currently pending; Bibliographic Data Only.

* cited by examiner

*Primary Examiner* — Dawayne A Pinkney

(57) ABSTRACT

An ophthalmic illuminator includes a one or more light combining stages arranged in series to augment a white light source with various color spectral bands. A first stage combines white light from a white light source with colored light from a first color source. Each subsequent stage in the series adds its own respective colored light. The color sources may be selectively turned on/off or driven with variable amounts of power. In this fashion, a combined light is produced by the final stage that represents a desired chromaticity and brightness as desired for a particular ophthalmic therapeutic procedure.

14 Claims, 3 Drawing Sheets

SPECTRALLY-ADJUSTABLE OPHTHALMIC ILLUMINATION WITH DISCRETE SOURCES

This application claims priority to U.S. Provisional Patent Application Ser. No. 61/349,316 filed on May 28, 2010.

TECHNICAL FIELD

This application relates to illumination in ophthalmic procedures and more particularly to ophthalmic illumination with spectrally-enhanced white light.

BACKGROUND

Ophthalmic illuminators allow a surgeon to illuminate the interior structure of the eye such as the vitreous and the retina during surgical procedures. For example, an endoscopic ophthalmic illuminator (endo-illuminator) includes an optical fiber within the bore of a cannula. By driving a proximal end of the optical fiber with a suitable light source, light emitted from a distal end of the fiber illuminates the desired portion of the eye during a surgical procedure. Alternatively, a physician may illuminate the eye with fiber optic illumination while using an ophthalmic microscope. With the desired portion of the eye sufficiently illuminated, the physician may then perform surgical procedures that may require the use of a vibrating cutting tool such as an ultrasonic handpiece to phacoemulsify a cataract-clouded lens or an oscillating cutter for vitrectomy procedures. Alternatively, the physician may perform laser photocoagulation therapy to address ocular conditions such as retinal detachments and tears as well as proliferative retinopathy resulting from diseases such as diabetes.

In general, it is desirable to minimize the optical fiber size used during illumination of ophthalmic therapeutic procedures so that corresponding incisions in the eye to admit the fiber can also be made as small as possible. Smaller incisions typically provide better therapy and recovery for the patient. But small fibers will necessarily have smaller etendue. In that regard, the amount of luminous flux or power (lumens) delivered by a fiber equals a product of the source brightness times the fiber etendue. Thus, a desirable decrease in fiber diameter also leads to an undesirable decrease in lumens delivered to the operating field in the eye. One cannot simply increase the number of sources to provide more lumens because of the conservation of etendue principle.

Another issue for ophthalmic illumination is the spectral output. In general, biological tissue is a broadband reflector such that white light illumination is preferable. However, there are situations such as the use of dyes or the detection of certain proteins in which a physician will prefer a suitably colored illumination. In general, most conventional white light sources such as a white light LED provide a fixed spectral output.

Accordingly, there is a need in the art for an improved ophthalmic illuminator that provides sufficient luminous power and also provides an adjustable spectrum.

SUMMARY

In accordance with a first aspect of the disclosure, an ophthalmic illuminator is provided that includes a white light source; and at least one combining stage, wherein each at least one combining stage includes a colored light source and a light combining member configured such that the white light source and the colored light source drive the light combining member to produce a combined light beam, and wherein each at least one combining stage is arranged from a first combining stage to a last combining stage such that the last combining stage produces a final combined light beam having a contribution from the white light source and from each color source.

In accordance with a second aspect of the invention, a method of spectrally adjusting light from a white light source is provided that includes the acts of driving the white light source to produce a white light; combining the white light with colored light from a first color source to produce a combined light; and illuminating at least a portion of an eye with the combined light.

In accordance with a third aspect of the invention, an ophthalmic illuminator is provided that includes a white light source; and a plurality of dichroic mirrors arranged from a first mirror to a last mirror such that the white light source transmits through the plurality of dichroic mirrors into a final combined light beam, and wherein each dichroic mirror associates with a corresponding light source having a unique spectral output such that the final combined light beam includes different spectral contributions from each of the corresponding light sources.

DESCRIPTION OF FIGURES

Embodiments of the present invention and their advantages are best understood by referring to the detailed description that follows. It should be appreciated that like reference numerals are used to identify like elements illustrated in one or more of the figures.

DETAILED DESCRIPTION

Figure 1:
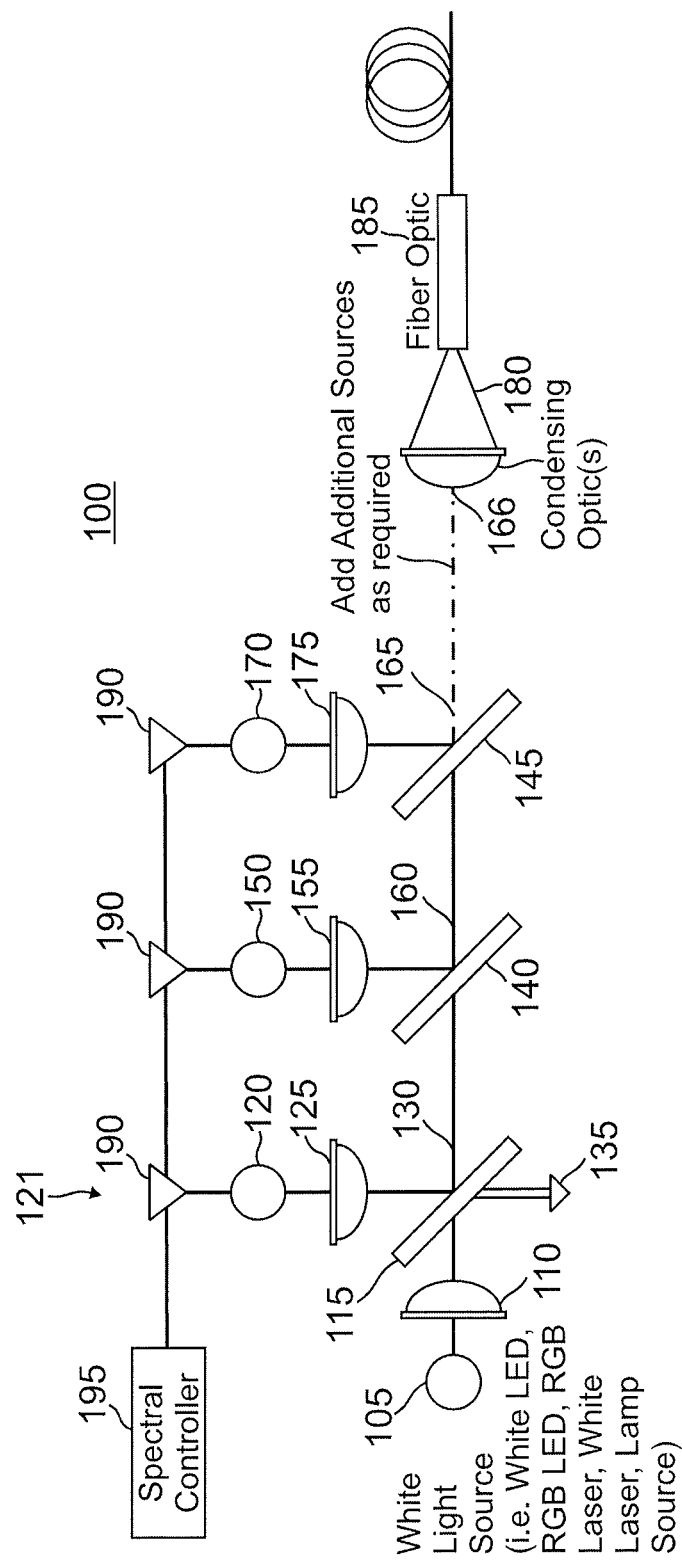
FIG. 1 illustrates an ophthalmic fiber optic illuminator including a plurality of individual colored light sources for selectively augmenting a white light source.

To provide spectral output selectivity and brightness flexibility, a white light source is advantageously augmented with variable amounts of one or more color spectral bands. In this fashion, a clinician may thus not only alter the spectral output for the illumination but may also vary (or keep constant) the resulting luminous flux despite the spectral augmentation. Turning now to the drawings, FIG. 1 illustrates an example spectrally-adjustable ophthalmic illuminator 100. A white light source 105 such as a white light emitting diode (LED), a red, green, and blue (RGB) combination of LEDs, a white laser, an RGB laser, or a white xenon, halogen, or a high-intensity discharge (HID) bulb is focused and/or collimated through optics 110 onto a light combining member such as a dichroic mirror 115. As known in the arts, dichroic mirror 115 will reflect a certain band of wavelengths yet be transparent to another set of wavelengths outside that band. Thus, dichroic mirror 115 is tuned so as to reflect the color band emitted by a color source 120 as focused and collimated through optics 125 onto dichroic mirror 115. The sources, mirror, and associated optics are aligned such that dichroic mirror 115 produces a first combined beam 130. In that regard, a spectral portion of light emitted by white light source 105 that is within the color band reflected by the dichroic mirror 115 will be reflected away from combined beam 130 as shown by hollow arrow 135. The remaining spectral portions in the white light emitted by white source 105 will pass through mirror 115 to combine with the reflected light from color source 120 to form first combined beam 130.

The spectral content for first combined beam 130 will thus be a sum of the contributions from white light source 105 and color source 120. For example, if dichroic mirror 115 is configured to reflect a red band of light such that color source 120 is a red source, first combined beam of light 130 will have a spectral power distribution that matches that produced by white source 105 outside the red spectral band. However, the spectral power for combined beam 130 within the red band reflected by dichroic mirror 115 will correspond to that provided by the red light source.

The combination of colored light source 120, optics 125 and dichroic mirror 115 may be considered to form a first combining stage 121. Other color bands may also be augmented using additional combining stages such as through dichroic mirrors 140 and 145. Each mirror is aligned to receive the combined light beam from the preceding combining stage. In that regard, each combining stage would comprise a corresponding colored light source, optics, and dichroic mirror. Each color source may comprise a color LED, color laser, or other suitable color source. Within each combining stage, the corresponding dichroic mirror will reflect light that corresponds to the color band transmitted by the combining stage's color source. For example, dichroic mirror 140 aligns with a color source 150 and optics 155 such that first combined beam 130 "combines" with the colored light reflected by dichroic mirror 140 to produce a second combined light beam 160. The quotations marks were used around "combines" in that the principle of conservation of etendue prevents a complete combination of first combined light beam 130 with the colored light from color source 150. Instead, as discussed analogously with regard to dichroic mirror 115, dichroic mirror 140 is configured to reflect that portion of light in first combined beam 130 that corresponds to the color band emitted by color source 150. Thus second combined beam 160 produced by dichroic mirror 140 will have a spectral power distribution that corresponds to the spectral power distribution for first combined beam 130 outside of the color band reflected by dichroic mirror 140. However, the spectral power distribution within this color band for combined beam 160 corresponds to that produced by color source 150. A similar combination of spectral powers occurs for a third combined beam 165 produced by dichroic mirror 145 as illuminated by a color source 170 (through optics 175) and second combined beam 160.

One can readily appreciate that any number of additional combining stages may be added to spectrally-adjustable illuminator 100. The dichroic mirrors within each stage may be replaced with other suitable light combining members. A resulting final combined beam 166 will thus have a spectral power distribution that represents a combination of the spectral power from white source 105 outside of those bands reflected by the various dichroic mirrors whereas the spectral power distribution for final combined beam 166 in the spectral bands reflected by the dichroic mirrors corresponds to the spectral power from the color sources in those spectral bands. Regardless of the total number of stages employed, final combined beam 166 is condensed through condensing optics 180 onto an optical fiber (or optical fiber bundle) 185 such that the resulting spectrally-adjusted light propagated through fiber 185 may be guided towards the desired portion of the eye to be illuminated.

To provide the clinician with the selectivity to adjust the spectral content of the resulting illumination, each color source may be switched on or off such that if a color source is turned on, it will contribute to the resulting combined beam. Alternatively, each color source may be driven by a variable power source such as variable current amplifiers 190 such that a clinician may vary the amount of power provided by respective color sources. For example, a clinician may command the desired spectral contribution through a spectral controller 195 such as a microprocessor that controls the gains applied by variable current amplifiers 190. Alternatively, spectral controller 195 may be programmed to automatically alter spectral contributions from the various color sources. Other suitable circuit architectures may be used for varying the color intensities. For example, the color sources may be driven by a modulated output from a constant power source. For example, variable pulse-width modulators may be coupled between the power source and a corresponding color source such that the desired intensity for a particular color band in the resulting illumination is achieved by varying the pulse width modulation for the corresponding color source.

Figure 2:
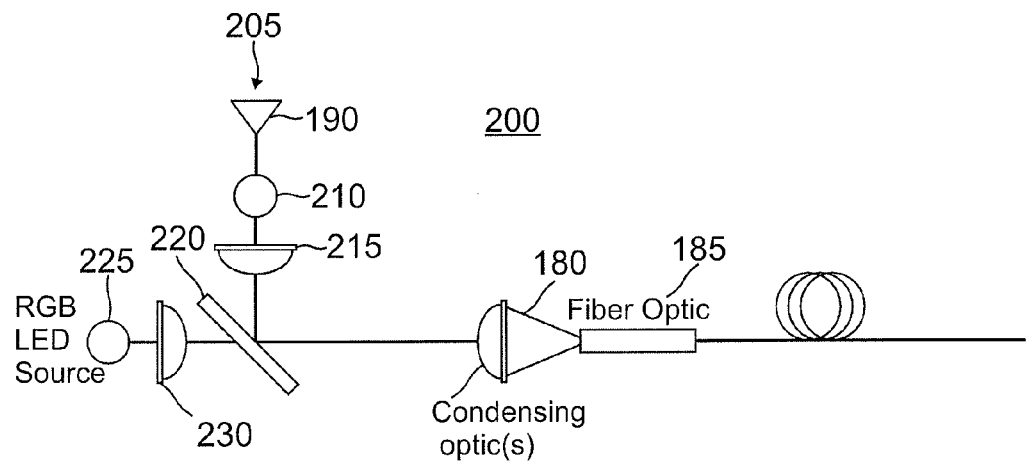
FIG. 2 illustrates an ophthalmic fiber optic illuminator including a red laser source for selectively augmenting a white light LED source.

Turning now to FIG. 2, an example ophthalmic illuminator 200 includes just a single combining stage 205 that includes a red laser source 210, optics 215, and dichroic mirror 220. An RGB LED source 225 provides the white light focused onto dichroic mirror 220 by optics 230. Although illuminator 200 thus includes just one combining stage, note that the red spectral power produced by conventional LED sources is presently a limiting factor for the resulting luminance for RGB LED sources. In that regard, if illuminator 200 did not include combining stage 205, the green and blue spectral powers provided by source 225 would have to be limited such that the resulting combined light from source 225 is suitably white within the desired chromaticity space. However, with combining stage 205, an inexpensive red laser diode source 220 may boost the spectral power in the red band such that the brightness for the resulting illumination from fiber 185 is increased while maintaining the desired chromaticity. In this fashion, illuminator 200 may achieve a suitable level of brightness even if fiber 185 is relatively thin despite the smaller entendue for such fibers.

Figure 3:
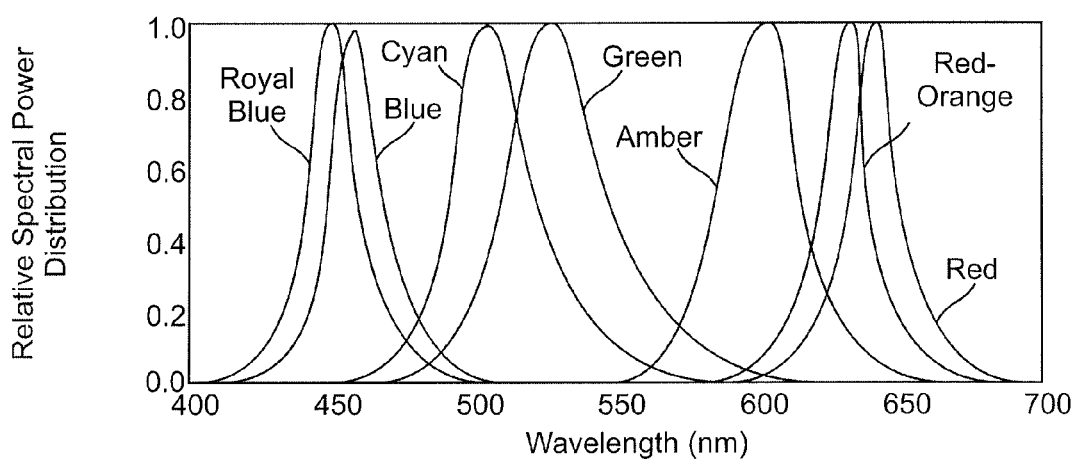
FIG. 3 illustrates the spectral power distribution bands for various color LED sources.
Figure 4:
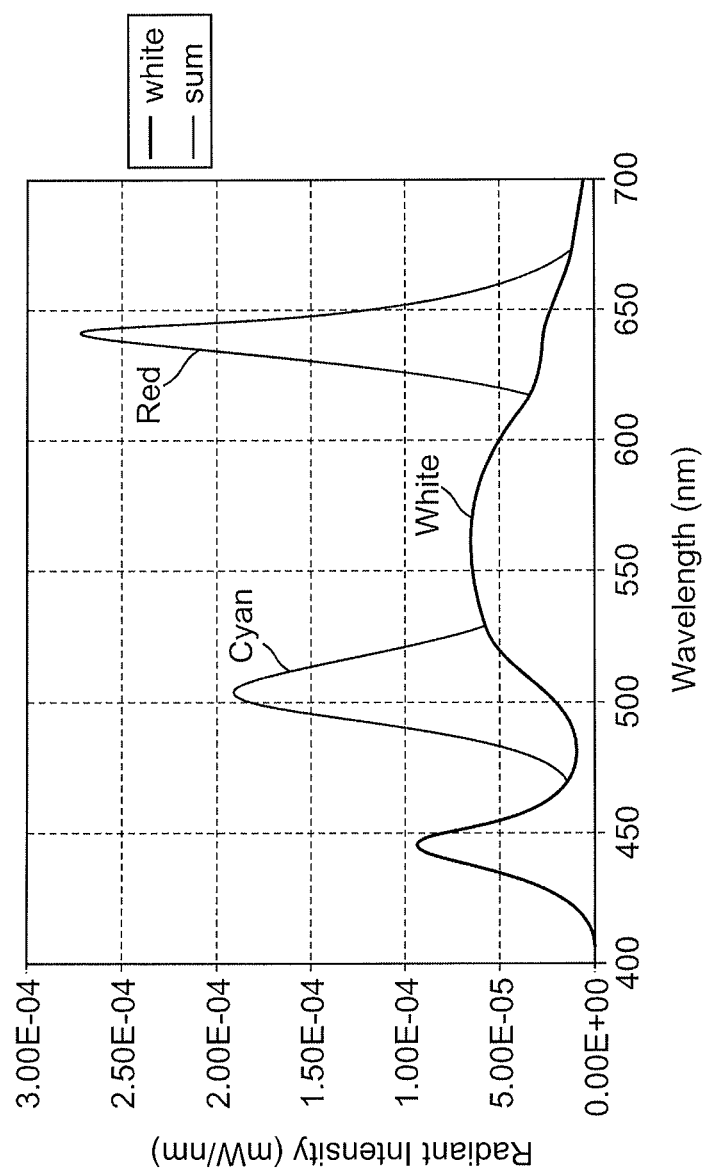
FIG. 4 illustrates the spectral power distribution for a spectrally adjustable illuminator.

Referring again to illuminator 100, a variety of suitable color sources is illustrated by FIG. 3. FIG. 3 shows the spectral power distributions for conventional LED sources. Each such color source could be combined with white light using the combining stages discussed herein. For example, FIG. 4 illustrates the resulting spectral power for an illumination produced by augmenting a white LED source using a cyan color combining stage and a red color combining stage. The resulting spectral power distribution thus corresponds to that provided by the red color combining stage within the red color band and to that provided by the cyan color combining stage within its color band (as determined by the corresponding dichroic mirror). Outside these two bands, the spectral power distribution corresponds to that originally provided by the white LED source. As discussed above, the color stages may be driven with a variable amount of power (and/or selectively turned on or off). The following table 1 shows the total luminous flux, the aphakic hazard, the x and y chromaticity coordinates for a CIE 1931 chromaticity color space diagram, and the (lumens/hazard watt) ratio according to various power combinations as applied to the color stages. In one configuration, only the white light source is driven. The first column of the table reflects such a white-light-only configuration. The second column for the table corresponds to a configuration in which the cyan combining stage is also driven at 100% of its power capacity. Finally, the third column corresponds to a configuration in which both the cyan and red combining stages are driven such that the cyan combining stage is driven at 100% of its power capacity and the red combining stage is driven at 30% of its power capacity. Note that such a contribution of red and cyan to the white light in the third configuration produces a suitable white chromaticity with notably higher total luminous flux yet less aphakic hazard than white light alone.

TABLE 1

|  | White Only | White + 100% Cyan | White + 100% Cyan + 30% Red |
|---|---|---|---|
| Total Luminous Flux (Lumens | 3.79 | 5.05 | 5.65 |
| Total Aphakic Hazard (normalized to 10 Lumens) | 6.61 | 6.16 | 5.52 |
| CIE 1931 Chromaticity x-coordinate | 0.3409 | 0.2865 | 0.3484 |
| CIE 1931 Chromaticity y-coordinate | 0.3699 | 0.4050 | 0.3876 |
| Lumens/Hazard Watt | 1512.2 | 1622.3 | 1811.2 |

Embodiments described above illustrate but do not limit the invention. It should also be understood that numerous modifications and variations are possible in accordance with the principles of the present invention. Accordingly, the scope of the invention is defined only by the following claims.

We claim:

1. An ophthalmic illuminator, comprising:
    a white light source;
    a plurality of combining stages comprising a red combining stage and a cyan combining stage, each combining stage comprising a colored light source and a light combining member comprising a dichroic mirror, the combining stages comprising:
        a first combining stage comprising a first dichroic mirror configured to combine a white light from the white light source with a first colored light from a first colored light source;
        one or more intermediate combining stages, each intermediate combining stage configured to combine light from a previous combining stage with an intermediate colored light from an intermediate colored light source; and
        a final combining stage configured to produce a final combined light beam having a contribution from the white light source and from each colored light source; and
    a spectral controller configured to control the colored light sources, but not the white light source, such that the cyan combining stage is driven at a greater percentage of its power capacity than that of the red combining stage to produce a white chromaticity with a higher total luminous flux and a lower aphakic hazard than that of the white light.

2. The ophthalmic illuminator of claim 1, further comprising:
    a condensing optic stage configured to condense the final combined light beam into a condensed light beam at least one optic fiber configured to receive the condensed light beam.

3. The ophthalmic illuminator of claim 1, wherein each colored light source is powered through a corresponding variable power amplifier.

4. The ophthalmic illuminator of claim 3, wherein each variable power amplifier comprises a variable current amplifier.

5. The ophthalmic illuminator of claim 1, wherein each combining stage includes optics to focus a colored light from the stage's colored light source onto the stage's dichroic mirror.

6. The ophthalmic illuminator of claim 1, wherein the white light source comprises an RGB LED.

7. The ophthalmic illuminator of claim 1, wherein the white light source comprises a white laser source.

8. The ophthalmic illuminator of claim 1, wherein each colored light source comprises a source selected from the group consisting of a color LED and a color laser diode.

9. The ophthalmic illuminator of claim 1, wherein the cyan combining stage is driven at 100% of its power capacity and the red combining stage is driven at 30% of its power capacity.

10. A method of spectrally adjusting light from a white light source, comprising:
    producing a white light at an illuminator comprising a plurality of combining stages comprising a red combining stage and a cyan combining stage;
    combining, using a first dichroic mirror of a first combining stage, the white light with colored light from a first colored light source to produce a first combined light;
    performing the following at each of one or more intermediate combining stages:
        combining light from a previous combining stage with an intermediate colored light from an intermediate colored light source of an intermediate combining stage;
    controlling, by a spectral controller, the colored light sources, but not the white light source, such that the cyan combining stage is driven at a greater percentage of its power capacity than that of the red combining stage to produce a white chromaticity with a higher total luminous flux and a lower aphakic hazard than that of the white light;
    producing a final combined light having a contribution from the white light source and from each colored light source; and
    illuminating at least a portion of an eye with the final combined light.

11. The method of claim 10, wherein illuminating a portion of the eye comprises illuminating the portion of the eye through at least one optic fiber.

12. The method of claim 11, wherein illuminating a portion of the eye comprises illuminating the portion of the eye through an optical fiber bundle.

13. The method of claim 10, further comprising varying a power driving the first colored light source to vary a spectral content of the final light.

14. The method of claim 10, wherein the cyan combining stage is driven at 100% of its power capacity and the red combining stage is driven at 30% of its power capacity.

* * * * *